(12) United States Patent
Burren et al.

(10) Patent No.: US 7,955,303 B2
(45) Date of Patent: Jun. 7, 2011

(54) INJECTION DEVICE WITH A TWO-WAY SLIP COUPLING

(75) Inventors: Stefan Burren, Bremgarten (CH);
Philippe Kohlbrenner, Kaltacker (CH);
Juergen Wittmann, Burgdorf (CH);
Martin Wittwer, Bowil (CH)

(73) Assignee: TecPharma Licensing AG, Burgdorf (CH)

( * ) Notice: Subject to any disclaimer, the term of this patent is extended or adjusted under 35 U.S.C. 154(b) by 0 days.

(21) Appl. No.: 12/047,043

(22) Filed: Mar. 12, 2008

(65) Prior Publication Data
US 2008/0306445 A1    Dec. 11, 2008

Related U.S. Application Data

(63) Continuation of application No. PCT/CH2006/000453, filed on Aug. 22, 2006.

(30) Foreign Application Priority Data

Sep. 14, 2005  (DE) .................. 10 2005 043 806
Dec. 20, 2005  (DE) .................. 10 2005 060 929

(51) Int. Cl.
*A61M 5/20*    (2006.01)
(52) U.S. Cl. ........................................ 604/136
(58) Field of Classification Search ............... 604/136, 604/135, 187, 134, 246
See application file for complete search history.

(56) References Cited

U.S. PATENT DOCUMENTS

| 6,004,297 | A | 12/1999 | Steenfeldt-Jensen et al. |
| 6,699,224 | B2* | 3/2004 | Kirchhofer et al. ........... 604/208 |
| 6,936,032 | B1* | 8/2005 | Bush et al. .................... 604/187 |
| 7,686,786 | B2* | 3/2010 | Moller et al. ................. 604/134 |
| 2002/0120235 | A1* | 8/2002 | Enggaard ...................... 604/135 |

FOREIGN PATENT DOCUMENTS

| DE | 10237258 A1 | 3/2004 |
| EP | 1351732 B1 | 6/2005 |
| WO | 01/72361 A | 10/2001 |

* cited by examiner

*Primary Examiner* — Nicholas D Lucchesi
*Assistant Examiner* — Brooke M Matney
(74) *Attorney, Agent, or Firm* — Dorsey & Whitney LLP; David E. Bruhn, Esq.

(57) ABSTRACT

An injection device including casing with a reservoir for an injectable product, an operating button which can be moved relative to the casing in a dosing direction which increases the dosage and in a correcting direction to set a product dosage, a conveying member for delivering the dosage set, a slip coupling comprising a latching element and a co-operating latching element which latch to each other in a latching engagement and couple the operating button to the casing in a positive and non-positive fit in discrete latching positions during a movement in the dosing direction or the correcting direction, and a spring member which opposes the movement of the operating button in at least one of the directions with a spring force, wherein the latching element or co-operating latching element are shaped such that in the latching engagement they offer a lower resistance to the movement in the at least one of the directions than to the movement in the other direction.

29 Claims, 5 Drawing Sheets

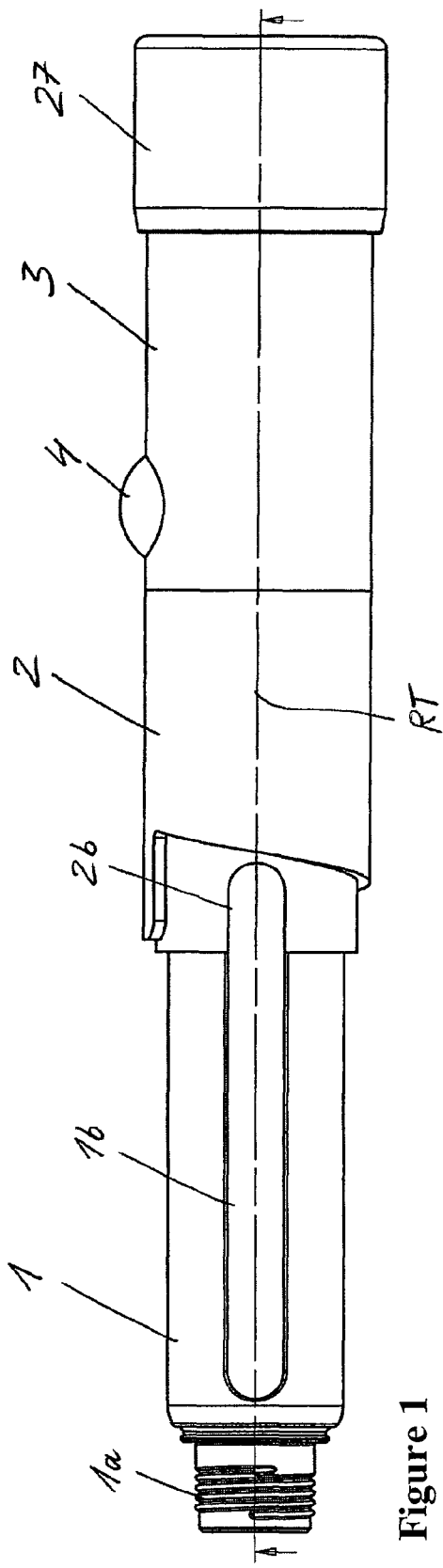
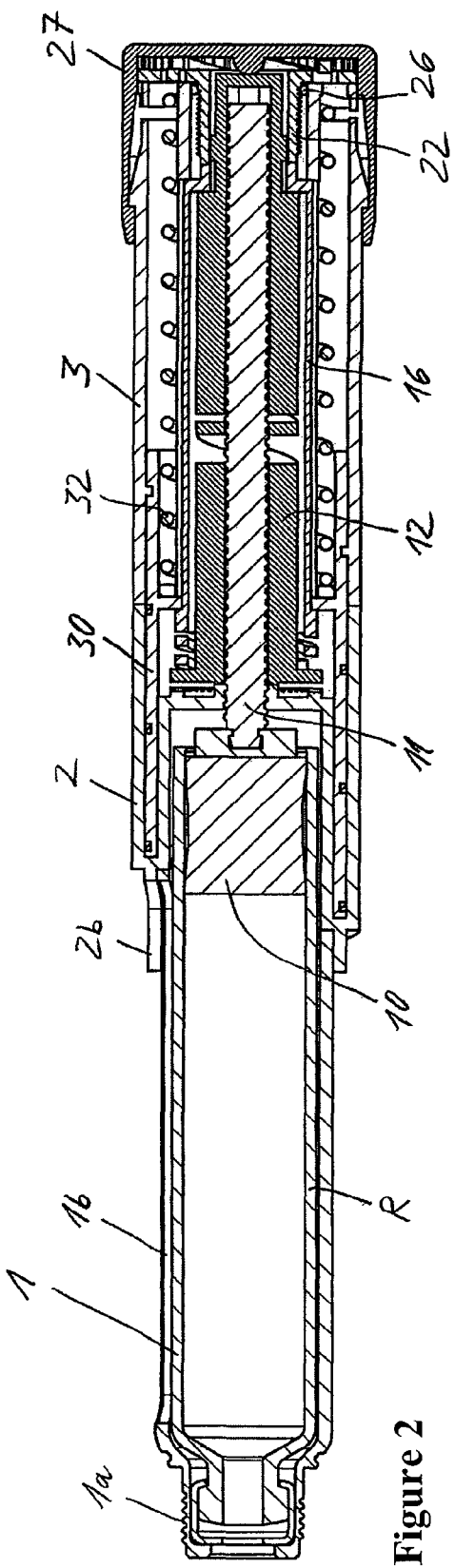
Figure 1
Figure 2

INJECTION DEVICE WITH A TWO-WAY SLIP COUPLING

CROSS-REFERENCE TO RELATED APPLICATIONS

This application is a continuation of International Application No. PCT/CH2006/000453 filed on Aug. 22, 2006, which claims priority to German Application No. DE 10 2005 043 806.7 filed on Sep. 14, 2005 and Germany Application No. DE 10 2005 060 929.5 filed on Dec. 20, 2005, the contents of all of which are incorporated in their entirety herein by reference.

BACKGROUND

The present invention relates to devices for injecting, administering, infusing, dispensing or delivering substances, and to methods of making and using such devices. More particularly, it relates to an injection device for an injectable product, e.g. a liquid medicine such as insulin, a growth hormone or an osteoporosis preparation.

EP 1 351 732 B1 discloses an injection device comprising a casing in which a reservoir for an injectable product and a conveying piston are arranged. A piston rod is in a threaded engagement with the casing. The device also comprises: a dosing member which can be axially moved relative to the casing and the piston rod in a threaded engagement with the piston rod; an operating button which can be rotated relative to the casing but cannot be axially moved and which is connected to the dosing member, secured against rotating; a coupling member which is connected to the piston rod such that it can be axially moved but is secured against rotating and which forms a two-way slip coupling with the dosing member; and lastly, a spring member which charges the coupling member with an elasticity force and thus holds it in a coupling engagement with the dosing member. The slip coupling is designed as a rotational slip coupling comprising two toothed rings which are in a latching engagement with each other which can be released against the force of the spring member and which thus form the coupling engagement. The latching engagement can be released in both rotational directions against the force of the spring member, such that the dosage can be increased by rotating the dosing member in one dosing direction and decreased by rotational slip coupling it in an opposite, correcting direction. In a dual function, the spring member acts as a coupling spring which tenses the coupling member into the coupling engagement with the dosing member, and as a delivery spring whose spring tension is increased by increasing the dosage during setting and which advances the piston during delivery. In order to prevent the coupling from inadvertently slipping while the dosage is being set, the toothed rings in the coupling engagement must withstand the spring tension. The force which the user must apply in order to increase the dosage is correspondingly high.

SUMMARY

It is an object of the present invention to provide an injection device which enables a dosage to be administered to be reliably set, including correcting the dosage, without having to apply a significant force.

In one embodiment, the present invention comprises an injection device for injecting a substance, and a method of making and using it, the injection device comprising a casing comprising a reservoir for the substance, an operating button for selecting a dosage of the substance to be injected, the button moveable relative to the casing in a first movement and a second movement, a slip coupling comprising co-operating latching elements engageable with each other and coupling the operating button to the casing in discrete latching positions during the movements of the button, and a spring member which opposes the movement of the operating button in at least one of the movements, wherein one of the latching elements is shaped such that when the elements are engaged there is a lower resistance to movement of the button in one of the movements than in the other movement.

In one embodiment, the present invention relates to an injection device comprising a casing with a reservoir for an injectable product, an operating button for setting a product dosage, a conveying member for delivering the dosage set, a two-way slip coupling and a spring member. To set the dosage, the operating button can be moved relative to the casing in a dosing direction which increases the dosage and a correcting direction which reduces the dosage. In some preferred embodiments, the operating button can be rotated relative to the casing. In other preferred embodiments, the operating button for setting the dosage can be only linearly movable or, in an alternative embodiment, linearly and rotationally movable relative to the casing. In some preferred embodiments, the casing and the dosing button each form a joint element of a jointly formed rotary joint. In principle, however, the dosing button can also be movably connected to the casing via one or more other joint elements and correspondingly via a plurality of joints. A conveying piston which is accommodated in the reservoir such that it can be linearly moved can expediently form the conveying member.

In some embodiments, the two-way slip coupling comprises at least one latching element and at least one co-operating latching element which latch to each other in a latching engagement and couple the dosing button to the casing in a positive and non-positive fit in discrete latching positions when the dosing button is moved in the dosing direction and correcting direction, respectively. The spring member opposes the movement of the dosing button in at least one of the two directions, e.g. the dosing direction, with an elastic spring force.

In accordance with the present invention, the latching element or the co-operating latching element is or are shaped in accordance with the spring force, such that in the latching engagement, they offer a greater resistance to the movement in the direction favored by the spring force than to the movement in the other direction. The word "or" is used here, as elsewhere, in its usual logical sense of "and/or", providing no other sense emerges from the respective context of the word's usage. The shape of the latching element or the co-operating latching element is selected such that the slip coupling offers a greater resistance to the movement of the operating button in the correcting direction than to the movement in the dosing direction, and due to its shape, the frictional resistance to be overcome to increase the dosage is lower than the frictional resistance to be overcome to correct the dosage.

In a preferred embodiment, the spring member is more highly tensed from latching position to latching position by the movement of the operating button in the at least one direction. Due to the shape of the latching element or co-operating latching element in accordance with the present invention, the coupling can be more reliably prevented from inadvertently slipping in the other direction, i.e. the direction in which the spring member acts, than in the prior art, while the resistance to the movement in the at least one direction due to the shape of the at least one latching element or co-operating latching element can simultaneously be less than in the case of a conventional slip coupling which is indifferent with respect to the movement direction. On the basis of the present invention, the force which has to be applied to set the dosage can be reduced as compared to the prior art, and the holding force of the coupling can still be increased. Equally, if the holding force remains the same, the force which has to be applied in order to set the dosage can be reduced, or if the force which has to be applied remains the same, the holding force of the slip coupling can be increased.

In one embodiment, the spring member can form a coupling spring, wherein the latching element and co-operating latching element are moved away from each other, both during the movement in the dosing direction and during the movement in the correcting direction, against the spring force of said coupling spring, to latch again in a next latching position. The spring force can be the same for both movement directions in each latching position. In some preferred embodiments, the spring member is more highly tensed from latching position to latching position during the movement in at least one of the directions, such that it opposes the movement in the relevant direction with a greater spring force than in the other, wherein it can also oppose the movement in the other direction with a spring force, albeit a smaller one.

In preferred embodiments, the spring member only opposes the movement in at least one of the two directions with a spring force. In such embodiments, the spring member does not serve as a coupling spring. Advantageously, a coupling spring is provided as an additional spring member, or a plurality of coupling springs are provided as additional spring members, in such embodiments, such that the latching element and co-operating latching element can be moved from latching position to latching position in both movement directions against the elasticity force of the separate coupling spring or the plurality of separate coupling springs. Functionally relieving the spring member in this regard offers greater design flexibility with regard to the shape and integration of the spring member. The spring member can also be more simply used in another additional function. The slip coupling can also be optimized by the at least one separate coupling spring or plurality of separate coupling springs with regard to its holding force and the force which has to be applied to overcome the holding force.

In some preferred embodiments, the spring member is a mechanical spring, but it can alternatively be a pneumatic spring. Depending on its function, the spring member may be a compression spring or a torsion spring, as applicable also a tension spring. In preferred embodiments, the conveying member can be driven by the spring member when delivering the dosage. In one preferred variant, the conveying member is driven only by the spring member during delivery. In a preferred second variant, the user must apply at least some of the force needed to drive the conveying member, and the conveying member fulfils the function of a servo-spring which assists the user, such that the user and the spring member share the force needed to drive the conveying member during delivery. A preferred example of the second variant is disclosed in German patent application No. 10 2005 043 806.7, which is hereby referenced.

The latching element and the co-operating latching element can be moved from latching position to latching position in a coupling dosing direction and a coupling correcting direction. In some preferred embodiments, the coupling dosing direction and the coupling correcting direction are opposite directions. The operating button is advantageously connected to one of the latching element and co-operating latching element, such that the coupling dosing direction corresponds to the dosing direction and the coupling correcting direction corresponds to the correcting direction of the operating button. In some embodiments, the one of the latching element and co-operating latching element is formed on or attached to the operating button, such that it moves with it, could be coupled to the operating button kinematically, i.e. slip-free, via one or more intermediate members. In such embodiments, the coupling dosing direction can deviate from the dosing direction of the operating button. The same applies to the coupling correcting direction and the correcting direction of the operating button. In some embodiments, however, the latching element moves relative to the co-operating latching element in the coupling dosing direction when the operating button is moved in the dosing direction, and moves in the coupling correcting direction when the operating button is moved in the correcting direction.

In some embodiments, the slip coupling comprises at least two coupling halves, namely a first coupling half comprising the at least one latching element and a second coupling half comprising the at least one co-operating latching element. The latching element and the co-operating latching element are formed on the respective coupling half in one piece, i.e. are connected to the assigned coupling half in a material fit or formed on it at the outset during the original molding process. Alternatively, they can also be attached to the respective coupling half. In some preferred embodiments, the slip coupling is a rotational slip coupling, wherein one of the coupling halves can be rotated relative to the other about a rotational axis, at least for setting the dosage. In some embodiments, the casing forms one of the coupling halves. A part which is separately manufactured but fixedly connected to a covering shell is regarded as being part of the casing. Alternatively, a structure which is connected to the casing, secured against rotating with respect to the rotational axis, but which can otherwise be moved relative to the casing, e.g. a structure which can be moved axially, can also form one of the coupling halves. In principle, both coupling halves can in fact be rotatable about the rotational axis relative to the casing, wherein, however, one of the coupling halves is connected to the casing, secured against rotating, or as applicable is coupled to the casing via a gear system, at least when setting the dosage. If a structure which is connected to the casing, secured against rotating, but which can be moved axially relative to the casing forms one of the coupling halves, it may be preferred that the operating button moves together with the axially movable structure in the axial direction, when setting the dosage and also during delivery, as is disclosed in German patent application No. 10 2005 043 806.7. The relative movement between the coupling halves can, in principle, be a rotation-free translational movement or a movement composed of a translation and a rotation. That which has been said above with respect to the rotational slip coupling for coupling one of the coupling halves to the casing also applies to such alternative relative movements between the coupling halves. Thus, the relative movement can, for example, be an axial linear movement parallel to a longitudinal axis of the injection device or a linear movement transverse to the longitudinal axis. Accordingly, one of the coupling halves can be formed or supported by the casing, a part connected to the casing such that it cannot move, or a part which cannot be moved relative to the casing in the direction of the relative mobility. That which has been said above with respect to the rotational slip coupling applies analogously to the alternative relative mobility instead of the relative rotational movement.

In some preferred embodiments, the slip coupling comprises exactly two coupling halves, i.e. in such embodiments, it consists of the coupling halves mentioned, and the latching element and the co-operating latching element engage with each other in a latching engagement. In alternative embodiments, the slip coupling comprises the two coupling halves and also a transmission member arranged between the coupling halves. The transmission member is in one latching engagement with a first coupling half of the two coupling halves and in another latching engagement with the second of the coupling halves; in some embodiments, it preferably forms a rotational slip coupling with each of the two coupling halves. Such a slip coupling is disclosed in DE 102 37 258 A1, which is hereby referenced in this respect. The slip coupling, comprising three elements in such alternative embodiments, comprises two pairs of at least one latching element and at least one co-operating latching element each. The first coupling half can be moved relative to the second coupling half, in a coupling dosing direction again and in an opposite coupling correcting direction, wherein in the latching engagement with the transmission member, it can be moved relative to the transmission member in one of these two directions, and when the transmission member is in latching engagement with the second coupling half, can be moved relative to the latter in the other direction, but only together with the transmission member.

In DE 102 37 258 A1 and also in German patent application No. 10 2005 043 806.7, the latching elements and co-operating latching elements of the two rotary grids axially engage with each other with respect to the rotational axis. Alternatively, however, the coupling halves and the transmission member arranged between them can also surround each other, e.g. coaxially, and the latching elements and co-operating latching elements can be formed on or attached to the circumferential surfaces which respectively face each other in pairs.

In some preferred embodiments, the at least one latching element or the at least one co-operating latching element is or are shaped asymmetrically with respect to the two directions in which they can be moved back and forth relative to each other. The asymmetry is such that a greater force has to be applied to move the operating button in the correcting direction than in the dosing direction. The resistance which has to be overcome when the latching element and co-operating latching element are in latching engagement is therefore greater in the correcting direction than in the dosing direction. The latching element and co-operating latching element, which represent a latching projection and a latching recess, comprise flanks with respect to the two directions of their relative mobility, wherein said flanks are asymmetrical with respect to the two directions, in that one flank of the latching element or co-operating latching element which points in one of the two directions is steeper than the flank of the same element which points in the other direction. In principle, it is sufficient if only the latching element or only the co-operating latching element is shaped asymmetrically, but in some preferred embodiments, a mutually adapted, congruent shape of the latching element and the co-operating latching element may be preferred.

The latching element and the co-operating latching element of the slip coupling, i.e. in one embodiment, the latching element and co-operating latching element of the coupling halves contacting each other and, in the alternative embodiment, the at least two pairs of the latching element and the co-operating latching element of the two coupling halves and of the transmission member, can be rigidly arranged on the coupling halves and the optional transmission member. In this case, at least one of the coupling halves or the optional transmission member as a whole is mounted such that it is elastically flexible against a spring force, so that the slip coupling can be moved in the latching engagement. In some preferred embodiments, however, the latching element or co-operating latching element is arranged on the relevant coupling half or the optional transmission member such that it is elastically flexible. In some embodiments, each latching element or co-operating latching element can form an elastic snapper, in that a coupling spring is provided for each latching element or co-operating latching element, from which the associated latching element projects or in which it is relieved as a latching recess. Although both the latching element and the co-operating latching element can each be formed as elastic snappers, in some embodiments only one of the latching element and the co-operating latching element is elastically flexible and the other is rigid.

In some embodiments, the coupling spring can be an elastic flexing strip which, on one hand, is clamped at one end only and projects freely from its clamp, e.g. in the circumferential direction about the rotational axis if the slip coupling is formed as a rotational slip coupling. In some preferred embodiments, the coupling spring is formed as a flexing strip which is clamped at both ends. To this end, the relevant coupling half can, for example, be shaped as a sleeve with an inner rotational axis, at least in a portion forming the latching element or co-operating latching element. To obtain the flexing strip, the sleeve is provided with a breach next to the flexing strip, next to which the flexing strip remains standing as a bridging element. This enables a plurality of flexing strips to be obtained in succession, with more rigid sleeve segments remaining between them, as viewed in the circumferential direction.

In some preferred embodiments, in which the spring member is tensed when the operating button is moved in the dosing direction and in which the spring energy absorbed when the dosage is being set solely drives or assists in driving the conveying member during delivery, the spring member advantageously acts directly, or, as applicable, via one or more intermediate members, on a dosing member which can be moved back and forth relative to the casing to set the dosage. During delivery, the dosing member is moved in one of the two directions of its mobility until it abuts a delivery stopper. In some preferred embodiments, it can also be moved in the other direction of its mobility until it abuts a maximum dosage stopper. The mobility of the dosing member can be a purely translational mobility or a purely rotational mobility; in some embodiments, it is both a translational and rotational mobility. Thus, the dosing member may be a joint element of a screw joint. If the dosing member can rotate, then at least one of the stoppers mentioned may be a rotational stopper.

Although it is in principle sufficient if the slip coupling only comprises a single latching element and a single co-operating latching element or, in embodiments with a transmission member, only two pairs each comprising only a latching element and a co-operating latching element, in some preferred embodiments a plurality of latching elements and a plurality of co-operating latching elements are provided for each latching engagement. In a respective latching engagement, it is also possible for only a single latching element to latch with a plurality of co-operating latching elements, i.e. with the respectively next co-operating latching element from latching position to latching position. The same applies analogously with regard to only a single co-operating latching element for each latching engagement. If a plurality of latching elements or co-operating latching elements are provided, it is sufficient with regard to the feature of their asymmetrical shape if only one of the elements exhibits this feature. In some preferred embodiments, all the latching elements or co-operating latching elements of the slip coupling are shaped in this way.

BRIEF DESCRIPTION OF THE DRAWINGS

FIG. 1 depicts one embodiment of an injection device in accordance with the present invention;

FIG. 2 shows the injection device in a longitudinal section;

DETAILED DESCRIPTION

Figure 3:
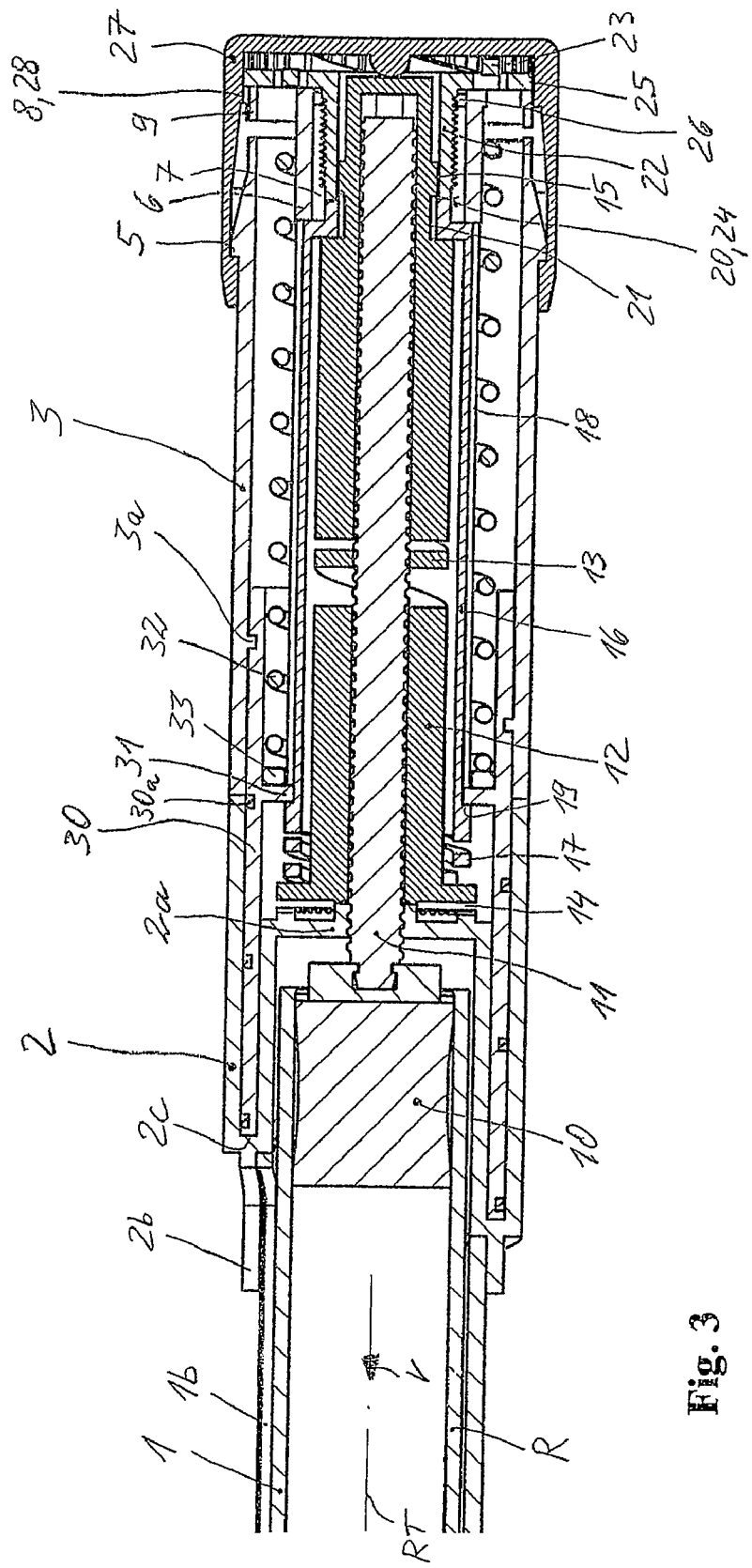
FIG. 3 shows the proximal portion of the injection device, in a longitudinal section.

FIG. 1 shows an embodiment of an injection device in accordance with the present invention in a lateral view. The injection device is formed as an elongated, slim injection pen. It comprises a casing including a distal (front or forward) casing portion 1 and a proximal (back or rear) casing portion which comprises two casing portions 2 and 3 which are fixedly connected to each other. The injection device serves to administer a liquid medicine, for example insulin. The medicine is contained in a reservoir which is inserted in the casing portion 1 and can be replaced. The medicine can be administered through an outlet 1a which is formed at the distal end of the casing portion 1. The injection device is substantially rotationally symmetrical with respect to a central longitudinal axis RT. The casing portions are each formed from a non-transparent plastic material. To enable the reservoir to be viewed, the casing portion 1 comprises a window 1b which extends to or near to the proximal end of the casing portion 1 and near to the outlet 1a, but which is comparatively narrow in the circumferential direction about the axis RT. The casing portion 2 also comprises a window 2b which overlaps with the window 1b when the casing portions 1 and 2 are connected, such that the view of the reservoir is also free in the region in which the casing portions 1 and 2 are connected. The windows 1b and 2b have the same width in the circumferential direction, although different dimensions in the circumferential direction would also be perfectly conceivable, providing at least the function of viewing the reservoir is still fulfilled. Another window 4, in the form of a magnifier, is formed in the casing portion 3. An operating button 27 forms the proximal end of the injection device. The operating button 27 fulfils the function of a manually operable dosing button which, when operated, can select and/or set a dosage of the medicine to be administered, and also fulfils the function of a trigger button which, when operated, delivers the dosage set. The dosage set can be read off through the window 4 on a dosage scale which passes underneath the window 4 during setting.

FIGS. 2 and 3 each show the injection device in a longitudinal section containing the longitudinal axis RT; FIG. 2 shows it as a whole and FIG. 3 shows the proximal portion in an enlarged representation.

The reservoir R is an ampoule made of glass or transparent plastic. A piston 10 is accommodated in the reservoir R such that it can be moved axially in an advancing direction V towards the outlet 1a. In the initial state shown in FIGS. 2 and 3, the reservoir R is completely full and the piston 10, which proximally seals the reservoir R, assumes its most proximal position. In principle, the casing portion 1 merely forms a reservoir holder. It is fixedly—but detachably, for replacing the reservoir 1—connected, for example screwed, to the casing portion 2.

The portions 2 and 3 which form the proximal casing portion are also fixedly connected to each other, e.g. in a material fit, and can functionally be regarded as a single casing portion. This casing portion mounts a dosing and advancing mechanism or means, by which a dosage of the medicine which can be delivered per injection can be set and by which the dosage set can be delivered by advancing the piston 10. To set the dosage, the operating button 27 is coupled to the dosing and advancing means by means of a dosing coupling.

The dosing and advancing mechanism comprises a plurality of members which are coupled to each other by the dosing coupling and a delivery coupling in different ways when setting the dosage and delivering the dosage. A piston rod 11 forms one of these elements. During delivery, the piston rod 11 presses against the rear side of the piston 10, such that the latter is moved in the advancing direction V and medicine is delivered through the outlet 1a. The piston rod 11 is in a threaded engagement with the casing portion 2, for which purpose it is provided with a thread over most of its length. The casing portion 2 forms the co-operating thread on a holding means 2a which projects radially inwardly towards the piston rod 11 (FIG. 3). The advancing movement of the piston rod 11 is a rotational movement about the longitudinal axis RT comprising a superimposed translation in the advancing direction V. The thread of the piston rod 11 is not formed circumferentially, but is rather interrupted by at least one axial flat side or groove. However, this does not interrupt the threaded engagement with the holding means 2a and the holding of the piston rod 11 in the threaded engagement.

The dosing and advancing mechanism or means also comprises a first coupling member 12, a second coupling member 16 and a third coupling member 22. The coupling member 12 is connected to the piston rod 11 such that it can be moved axially along its flat side or groove in a guiding engagement but is secured against rotating. The coupling member 12 is proximally arranged with respect to the holding means 2a and presses against the holding means 2a in the advancing direction V. The coupling member 12 surrounds the piston rod 11. The coupling member 12 comprises a distal portion which contacts the holding means 2a, and a proximal portion which extends up to the operating button 27. A spring 13 is formed between the two portions. At the distal end of the coupling member 12, another spring 14 is formed which comprises a plurality of spring tabs which project towards the holding means 2a and are elastically tensed. The spring tabs of the spring 14 form latching elements which latch with co-operating latching elements of the holding means 2a, such that a rotational slip coupling is obtained between the coupling member 12 and the holding means 2a and therefore the casing portion 2, wherein said rotational slip coupling prevents the piston rod 11 from rotating relative to the casing 1-3 if jolted. However, the force which can be transmitted when the latching elements and co-operating latching elements of the rotational slip coupling are in the coupling engagement is not large enough to prevent—or obstruct to any practical degree—the rotational movement of the piston rod 11 needed to deliver the dosage set. The coupling member 12 can axially flex in the portion of the spring 13. The coupling member 12, including the two springs 13 and 14, is molded from plastic in one piece, e.g. in an injection-molding process.

The coupling member 16 is mounted such that it can be rotated about the axis RT. It is sleeve-shaped and surrounds the coupling member 12. At the distal end of the coupling member 16, a spring 17—in the exemplary embodiment, an axially short helical spring—is formed in one piece. The coupling member 16 is supported in the distal direction on the coupling member 12 via its spring 17 and presses the coupling member 12 against the holding means 2a. Engaging elements 20 are formed on the proximal end of the coupling member 16 and—in the state of the injection device shown—are in a releasable coupling engagement with co-operating engaging elements 24 of the coupling member 22. The engaging elements 20 and co-operating engaging elements 24 can be teeth which axially project from one of the coupling members 16 or 22 towards the other and form two toothed rings which are concentric with respect to the axis RT, engage with each other in the coupling engagement, and have a uniform tooth separation, as shown by way of example in FIG. 4. In the state shown, in which the user can set the dosage to be administered, the engaging elements 20 and co-operating engaging elements 24 of the two coupling members 16 and 22 engage with each other. The coupling members 16 and 22 form the dosing coupling and are connected to each other, secured against rotating, in the coupling engagement.

Figure 4:
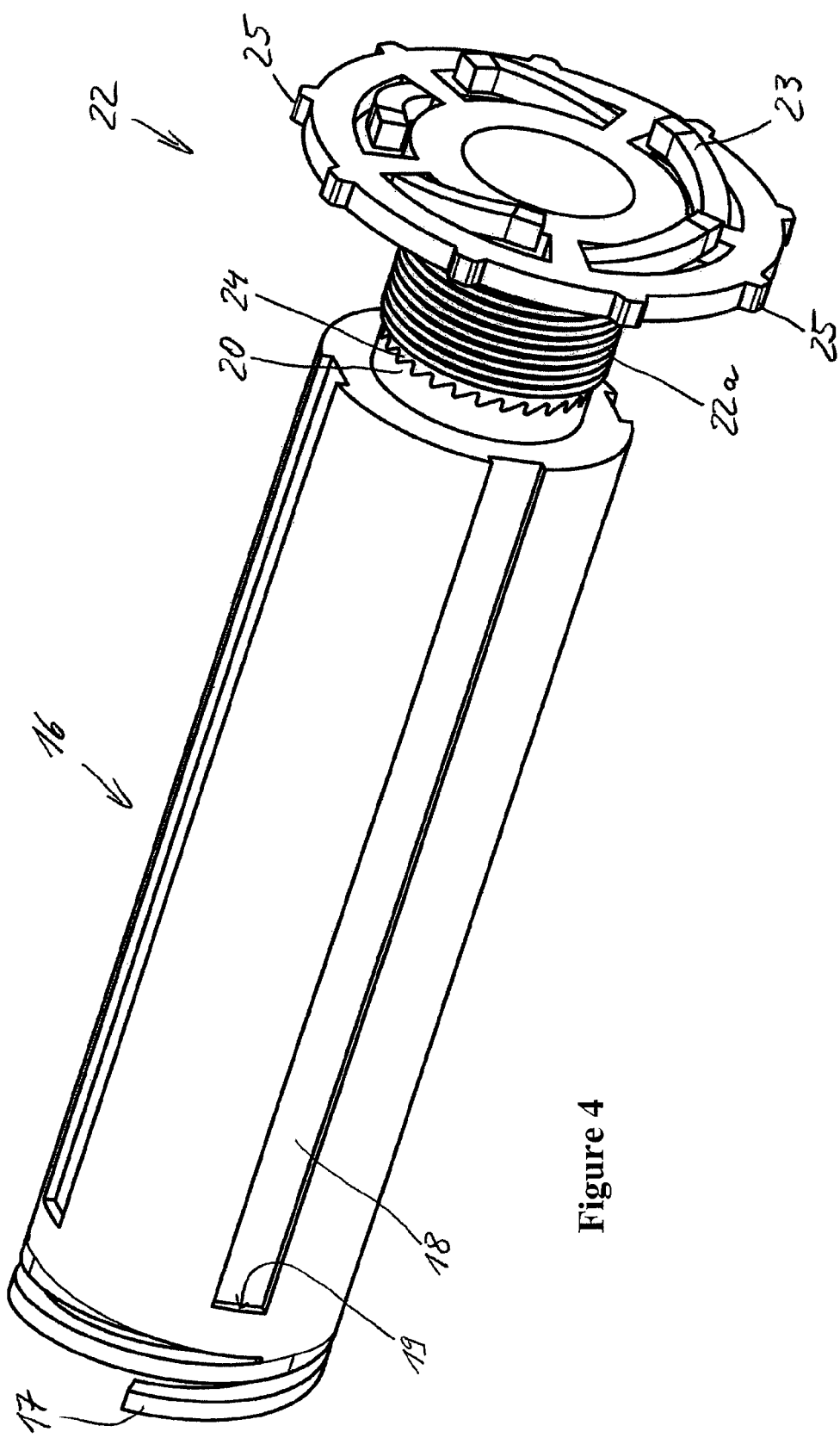
FIG. 4 depicts an embodiment of a dosing coupling in a coupling engagement.

FIG. 4 shows the coupling halves of the dosing coupling, i.e. the coupling members 16 and 22, in a coupled engagement and removed from the overall context, such that their functional elements 17-20 on the one hand and 23-25 on the other hand can be clearly seen.

The coupling member 22 is also sleeve-shaped and comprises a flange at its proximal end which projects radially outwardly. Engaging elements 25 are formed on the outer circumference of the flange and connect the coupling member 22, secured against rotating, to the operating button 27. The coupling member 22 is axially supported on the operating button 27 via a spring 23. The spring 23 is an integral part of the coupling member 22, in that the coupling member 22—including the spring 23—is molded from plastic in one piece. Like the spring 14, the spring 23 consists of a plurality of axially projecting spring tabs which are bent about the axis RT. In conjunction with the spring 17, it ensures that the coupling members 16 and 22 are axially held elastically in the coupling engagement. The spring 17 also presses the coupling member 16, and the spring 23 the coupling member 22, axially against the casing portion 3 up to a stopper.

The coupling member 22 is in a threaded engagement with a stopper member 26. To this end, the coupling member 22 is provided with a thread 22a on its outer circumference upstream of the flange (FIG. 4). The casing portion 3 forms an axial guide 7 for the stopper member 26, opposing the thread 22a radially outwardly, such that the stopper member 26 is axially moved in the threaded engagement when the coupling member 22 is rotated. The axial adjusting path of the stopper member 26 corresponds to the maximum quantity of the medicine which is available, i.e. when the reservoir R is full, and administered in a plurality of injections. When the coupling member 22 is rotated, the stopper member 26 travels—guided by the axial guide 7—along the outer thread 22a of the coupling member 22 in the axial direction; in the exemplary embodiment, the advancing direction V. When the stopper member 26 has reached an axial stopper formed by an inner sleeve 6 in this movement direction, this means that the reservoir R has been completely emptied. The inner sleeve 6 forms the axial guide 7 and cannot be moved axially relative to the casing portion 3; in the exemplary embodiment, it is formed by a radial connecting stay on the casing portion 3, i.e. it is part of the casing portion 3.

The dosing and advancing means also comprises a dosing and display member 30 which is in a threaded engagement with the casing portion 3. For the purpose of this threaded engagement, the casing portion 3 is provided with an inner thread 3a. The casing portion 2 is smooth in its contact region with the dosing and display member 30. The thread 3a is formed directly on the inner surface area of the circular-cylindrical covering shell of the casing portion. The dosing and display member 30 is substantially a simply circular-cylindrical sleeve with a correspondingly shaped outer thread 30a. The threads 3a and 30a have a significantly larger thread pitch than the threads of the piston rod 11 and the holding means 2a. The thread pitch is large enough to prevent self-locking in the threaded engagement, and the dosing and display member 30 is rotated and axially moved relative to the casing portion 2, 3 by a purely axial force in the threaded engagement.

The dosing and display member 30 is coupled to the coupling member 16 such that it can be moved axially but is secured against rotating. In the exemplary embodiment, the dosing and display member 30 and the coupling member 16 are directly in a corresponding guiding engagement with each other. To this end, the coupling member 16 forms an axial guide 18 on its outer circumference. A projecting engaging element 31 is formed on the inner surface area of the dosing and display member 30, via which the dosing and display member 30 is in guiding engagement with the coupling member 16, i.e. with its guide 18. The guide 18 extends over most of the length of the coupling member 16, and the dosing and display member 30 passes over most of its length when the maximum dosage is set. The guide 18 is formed by axial grooves in the outer surface area of the coupling member 16 (FIG. 4). At their distal ends, the grooves each form a stopper 19 for the engaging element 31.

The dosing and advancing means further comprises a spring member 32 which charges or urges the dosing and display member 30 with a force in the distal direction. The spring member 32 of the exemplary embodiment is a helical spring and acts as a compression spring. The spring member 32 is supported on the casing portion 3b in the proximal direction. In the distal direction, the spring member 32 is supported on an annular sliding disc 33 which is inserted between the coupling member 16 and the dosing and display member 30 and supported for its part on the engaging element 31. By the sliding disc 33, the spring member 32 is largely decoupled from rotational movements of the dosing and display member 30.

The dosing and display member 30 can be moved back and forth between axial end positions relative to the piston 10 and the piston rod 11 and also to the coupling members 12, 16 and 22. The two end positions are a zero dosage position and a maximum dosage position. The two end positions are each predetermined by a stopper. The stopper for the zero dosage position is formed as an axial stopper by a shoulder 2c at the distal end of the casing portion 2. The stopper for the maximum dosage position is formed by the casing portion 3. In the zero dosage position, a distal portion of the dosing and display member 30 overlaps the reservoir R in the advancing direction V up to and beyond the piston 10 when the piston 10 assumes a rearmost position in the reservoir R, as shown in FIGS. 2 and 3. The piston 10 assumes this position when the reservoir R is completely full. The thread 30a extends up to the distal end or at least near to the distal end of the dosing and display member 30, such that the thread 30a also axially overlaps the reservoir R and the piston 10 when the dosing and display member 30 assumes the zero dosage position. The thread 30a terminates before the distal end of the dosing member 30 and, together with the thread 3a of the casing portion 3, forms a rotational stopper which defines the maximum dosage position of the dosing and display member 30. Alternatively, the thread 30a could also taper off at the distal end of the dosing and display member 30; in such a modification, the stopper defining the maximum dosage position would then have to be formed another way.

At or near its distal end, the dosing and display member 30 is not fully cylindrical in its circumference, but rather only partly cylindrical, to offer a view onto the piston despite the axial overlap, even if—as may be preferred—the dosing and display member 30 is not formed from a transparent plastic but rather from a non-transparent or at least opaque plastic material or other material. The distal edge of the dosing and display member 30 extends in a spiral about the axis RT, such that—as can be seen in FIGS. 2 and 3—one circumferential region of the distal end of the dosing and display member 30 even protrudes axially beyond the piston 10, and another circumferential region, which overlaps the window in the zero dosage position, is short of the piston 10, such that the piston 10 can be viewed through the windows 1b and 2b. Instead of a spiral edge, the dosing and display member 30 can circumferentially extend to the same axial height all over, except for example for a breach, and so extend beyond the piston 10 in the advancing direction V all over, except for the breached region, wherein the breach would overlap the window 2b in the zero dosage position. The shoulder 2c of the casing portion 2 is also wound about the axis RT, following the spiral course of the distal edge of the dosing and display member 30. The winding course of the shoulder 2c can also be seen in FIG. 1. The casing portion 2 comprises an outer sleeve which, together with the casing portion 3, encloses the dosing and advancing means, and an inner sleeve which is connected to the outer sleeve at its distal end by a stay forming the shoulder 2c, and at the proximal end of which the holding means 2a projects radially inwardly. An annular gap remains between the outer and the inner sleeve, into which the dosing and display member 30 protrudes over most of its length in the zero dosage position, wherein the larger part in the region of the longest circumferential segment of the dosing and display member 30 accounts for approximately 50% of the total length of the dosing and display member 30.

The dosing and display member 30 is the carrier for a dosage scale which extends in a spiral around the outer circumference of the dosing and display member 30 with a pitch, as measured with respect to the axis RT, which corresponds to the pitch of the thread 30a. The dosage scale consists of markings and numbers, wherein each of the markings corresponds to the smallest dosage unit which can be set. When setting the dosage to be administered, the dosage scale can be read off through the window 4 of the casing portion 3 (FIG. 1).

The operating button 27 forms the proximal end of the injection device. It is clipped to the casing portion 3, by providing the casing portion 3 with a shoulder 5 at its proximal end, which grips behind the operating button 27. The operating button 27 can be rotated relative to the casing portion about the axis RT, in a dosing direction and a correcting direction. When setting the dosage, the dosage is increased by rotating the operating button 27 in the dosing direction and reduced when it is rotated in the correcting direction, enabling a dosage which has inadvertently been set too high to be corrected. The operating button 27 is also connected to the coupling member 22, such that it can be axially moved but is secured against rotating by the engaging elements 25.

Figure 5:
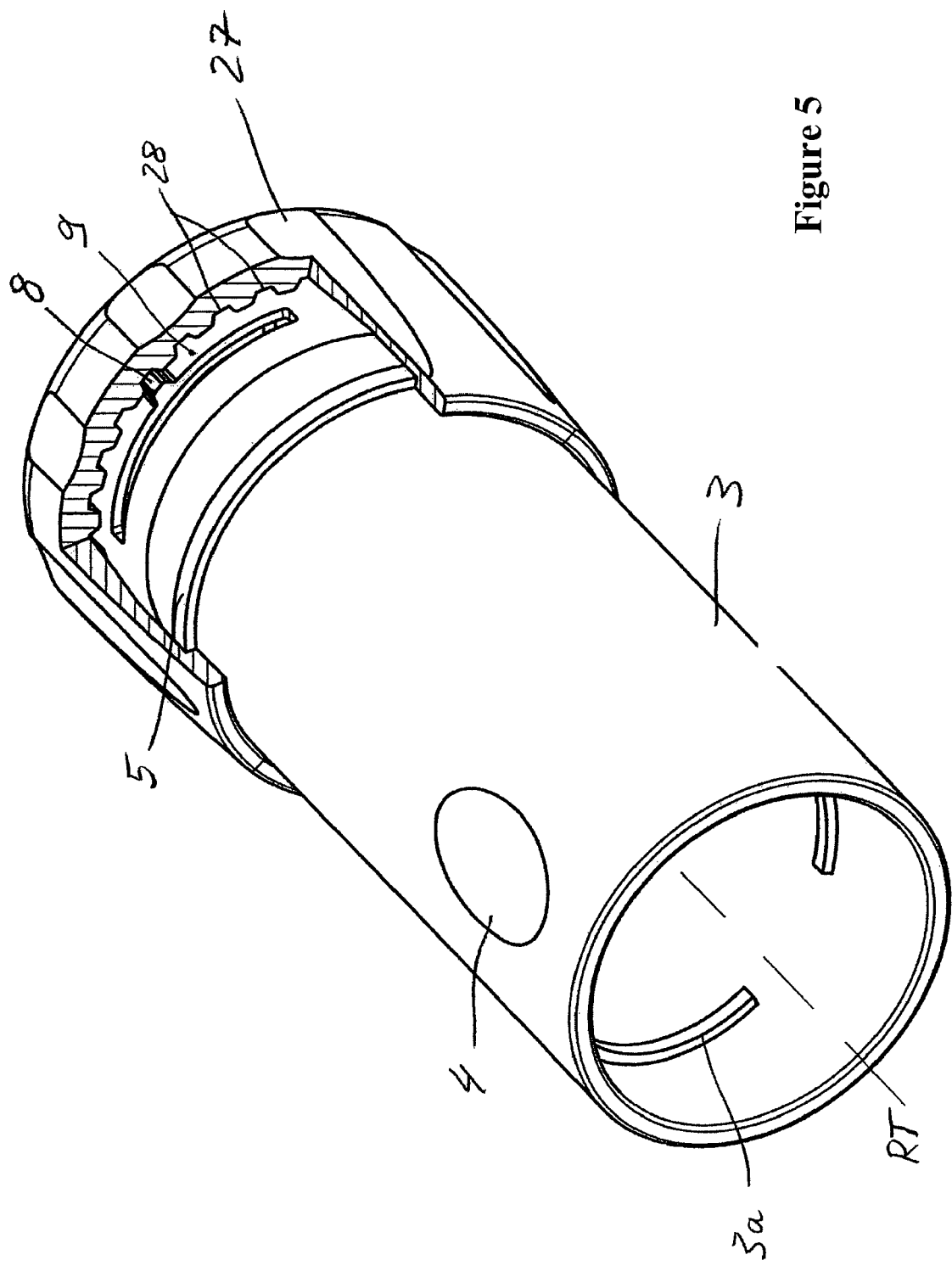
FIG. 5 depicts an embodiment of a casing portion and an operating button.

FIG. 5 shows the casing portion 3 and the operating button 27 in coupling engagement, wherein a part of the operating button has been cut away to show the engagement.

The operating button 27 forms a slip coupling—in the exemplary embodiment, a rotational slip coupling—with the casing portion 3, beyond the rotational block with the coupling member 22. To form the slip coupling, a plurality of latching elements 28 are formed on the operating button 27 in a uniform distribution about the axis RT and are in a coupling engagement with corresponding, e.g. congruent, co-operating latching elements 8 formed at the distal end of the casing portion 3. The number of co-operating latching elements 8 is lower than the number of latching elements 28. The operating button 27 can be rotated about the axis RT relative to the casing portion 3 when the latching elements 28 and co-operating latching elements 8 are in coupling engagement, wherein the latching elements 28 and co-operating latching elements 8 releasably latch to each other in pairs in latching positions discretely distributed around the circumference. The separation of the latching elements 28 and thus the distance as measured as angles or arcs between each of the latching elements 28 which are immediately adjacent in the circumferential direction corresponds to the smallest dosage unit which can be set, and the separation of the co-operating latching elements corresponds to an integer multiple of the same dosage unit. The slip coupling does not necessarily have to be formed directly between the casing 1-3 and the operating button 27. Instead of providing the latching elements 28 on the operating button 27, they could also be formed on the coupling member 22. In both embodiments, modified latching elements and co-operating latching elements could, for example, engage axially with each other, instead of radially.

The latching elements 28 and, correspondingly, the co-operating latching elements 8 are asymmetrical in shape with respect to the rotational direction, such that the force which has to be applied in a coupling dosing direction to release the latching engagement is greater than in the opposite rotational direction, i.e. the coupling correcting direction. Since, in the exemplary embodiment, the operating button 27 itself directly forms the latching elements 28, the dosing direction of the operating button 27 is simultaneously also the coupling dosing direction, and the correcting direction is simultaneously also the coupling correcting direction. The co-operating latching elements 8 are latching cams which project radially outwardly from the outer surface area of the casing portion 3. The latching elements 28 are correspondingly formed on the oppositely facing inner surface area of the operating button 27 as corresponding recesses or tooth gaps of inner teeth. To achieve asymmetry with respect to the two rotational directions, the leading flanks of the latching elements 28 pointing in the coupling dosing direction are flatter than the trailing flanks pointing in the opposite rotational direction—the coupling dosing direction when the latching elements 28 are moved. The co-operating latching elements 8 are correspondingly formed with both sides nestled.

The asymmetry of the slip coupling with respect to the two rotational directions of the operating button 27 is adapted to the direction of the force exerted by the force member 32 on the dosing and display member 30. For when the operating button 27 is rotated in the direction of increasing the dosage, i.e. upping the dosage, the dosing and display member 30 is rotated in the threaded engagement, via the dosing coupling formed at and the guiding engagement formed at 18 and 31, and moved in the proximal direction. In the course of translation in the proximal direction, the spring member 32 is increasingly tensed. The elasticity force of the spring member 32 offers a resistance to the movement of the dosing and display member 30 in the proximal direction, which acts on the slip coupling via the coupling described and offers the rotational movement of the operating button 27 in the dosing direction, in which the flatter flanks of the latching elements 28 and co-operating latching elements 8 point, an additional frictional resistance which increasing as the dosage is upped. Conversely, the force exerted by the spring member 32 assists the rotational movement in the direction of a dosage correction.

FIG. 5 shows the casing portion 3 and its co-operating latching elements 8 for the slip coupling. In a proximal sleeve portion, the casing portion 3 forms radially and elastically flexible coupling springs 9, one for each co-operating latching element 8. The co-operating latching elements 8 each project radially outwardly from their coupling springs 9. The coupling springs 9 are ring segments. Circumferentially around the axis RT, the sleeve portion is alternately composed of the coupling springs 9 and comparatively stiffer ring segments. The coupling springs 9 each act as flexing strips which extend in the circumferential direction and are clamped at both ends, namely at the two more rigid ring segments which are immediately adjacent to each other. A cavity extends in the circumferential direction along each of the coupling springs 9, which increases the flexibility of the respective coupling spring 9. The sleeve portion forming the coupling springs 9 forms the proximal end of casing portion 3.

The operating button 27 is cup-shaped with a base which forms the distal end of the injection device and a wall which projects from the base and encircles the axis RT, and on the inner area of which the latching elements 8 are arranged in uniform distribution around the circumference, respectively formed as axially extending recesses. When assembled, the latching elements 28 are in engagement both with the co-operating latching elements 8 and the engaging elements 25 (FIG. 3) of the coupling member 22, wherein both the latching engagement with the co-operating latching elements 8 and the rotational block engagement with the engaging elements 25 is maintained in every axial position of the operating button 27.

Figure 6:
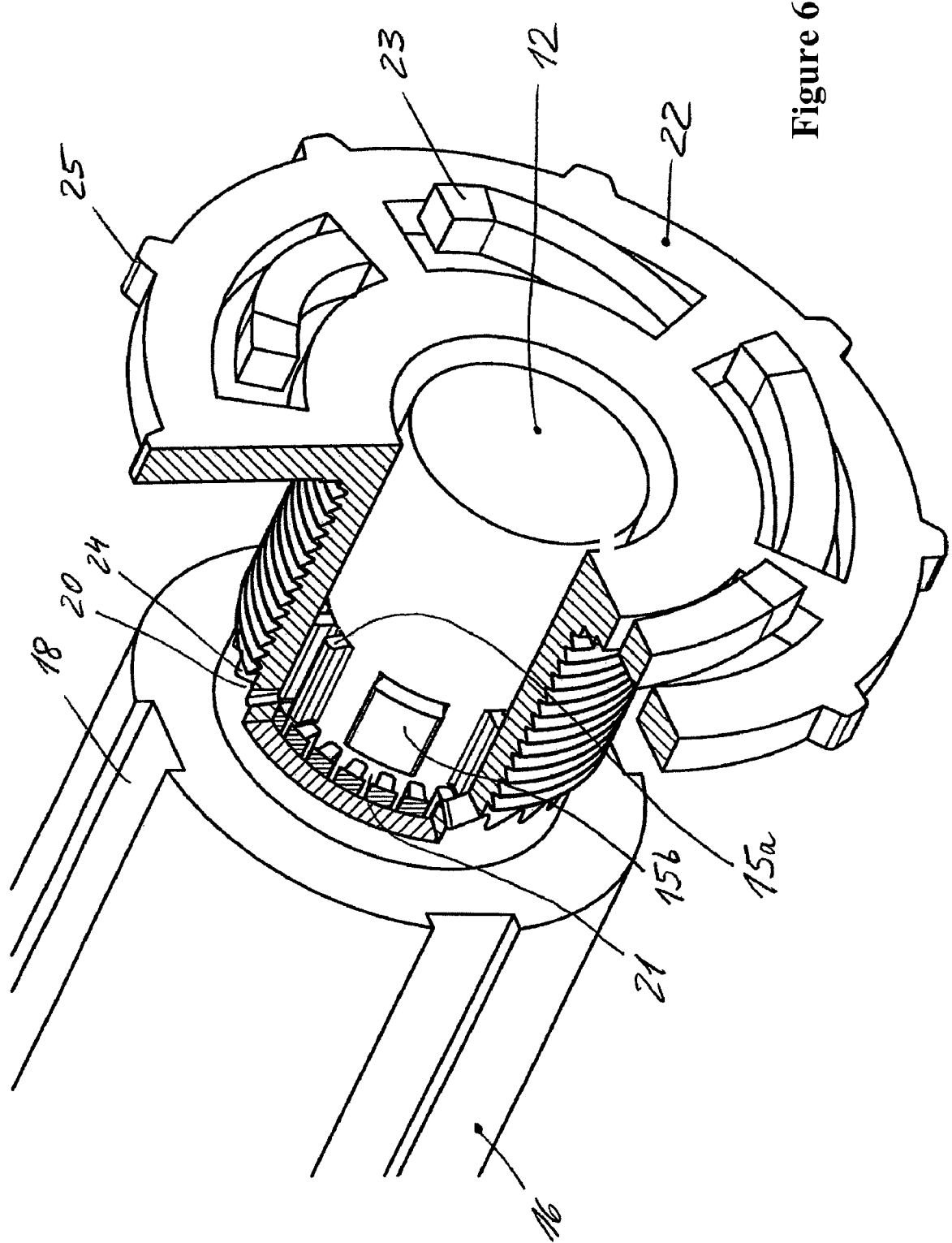
FIG. 6 depicts an embodiment of a disengaged delivery coupling.

In addition to the dosing coupling formed by the coupling members 16 and 22, the dosing and advancing mechanism or means contains a second coupling, namely the delivery coupling already mentioned which is shown in FIG. 6. The delivery coupling is formed by the coupling members 12 and 16, which are provided for this purpose with engaging elements which engage with each other in the coupling engagement. On the side of the coupling member 12, these are engaging elements 15*a* and 15*b*. The coupling member 16 is provided with co-operating engaging elements 21. The engaging elements 15*a* are axial ribs which project radially outwardly at the proximal end from an outer surface area of the coupling member 12. The co-operating engaging elements 21 are correspondingly formed on an inner surface area at the proximal end of the coupling member 16 as axial blind grooves. The co-operating engaging elements 21 form an axial guide for the engaging elements 15*a*. The engaging elements 15*a* form a sort of outer teeth about the axis RT. The outer toothed area or teeth are interrupted at least at one location and, in the exemplary embodiment, at two diametrically opposite locations. One of the respective engaging elements 15*b* is formed in the interrupted circumferential region. Like the engaging elements 15*a*, the engaging elements 15*b* project radially outwardly, but are wider than the engaging elements 15*a* in the circumferential direction, such that they cannot enter the engaging elements 21 formed as blind grooves. Rather, the rib stays remaining between the engaging elements 21 form an axial stopper for the engaging elements 15*b* when the coupling member 12 is moved in the distal direction relative to the coupling member 16.

The coupling member 16 is selectively in a coupling engagement with the coupling member 22 or the coupling member 12, i.e. in coupling engagement with the coupling member 22 when the delivery coupling is released and in coupling engagement with the coupling member 12 when the dosing coupling is released. To set the dosage, the dosing coupling is closed, i.e. the engaging elements 15*a* and 15*b* only axially overlap the coupling member 22, the inner surface area of which is however circumferentially smooth, such that the coupling member 22 can rotate relative to the coupling member 12 when setting the dosage. To deliver the dosage set, the coupling member 12 moves into coupling engagement with the dosing and display member 30, which releases the dosing coupling and closes the delivery coupling, such that the delivery can begin. FIG. 6 shows the coupling members when the dosing coupling is closed.

The following explains how the device may be used:

The user holds the injection device in one hand and fits a cannula unit onto the outlet 1*a* and screws it on tight with the other hand. The injection device is otherwise in the state shown in FIGS. 1 to 3. The user can verify the level of the reservoir R or position of the piston 10 through the windows 1*b* and 2*b*. It is assumed that he has already primed the reservoir R and wishes to inject himself in the next step with a particular dosage of the medicine. By turning the operating button 27, he sets the desired dosage. While setting the dosage, he can read the current dosage, corresponding to the axial position of the dosing and display member 30, through the window 4. If, while upping the dosage, he inadvertently selects a dosage which too high, he can correct the excess dosage by turning the operating button 27 in the correcting direction. While setting the dosage, the rotational movement of the operating button 27 is transmitted onto the coupling member 22 via the rotational block at 25, onto the coupling member 16 via the closed dosing coupling and onto the dosing and display member 30 in the guiding engagement between 18 and 31. In the engagement between the threads 3*a* and 30*a*, the dosing and display member 30 moves rotationally about the axis RT and translationally in the proximal direction. While upping the dosage, the spring member 32 is increasingly elastically tensed and assists any dosage correction to be made as applicable. Both while upping the dosage and correcting the dosage, the latching engagement of the slip coupling between the casing portion 3 and the operating button 27 generates a clearly perceptible clicking noise. Due to the steepness of the threads 3*a* and 30*a*, the dosing and display member 30 travels a correspondingly long adjusting path in the axial direction. The distances between the dosage marks on the dosage scale of the dosing and display member 30 are correspondingly large in the axial direction, such that an unambiguous reading of the dosage mark currently passing underneath the window 4 is ensured, even for visually impaired users.

The piston rod 11 is decoupled from the dosing movement—in the exemplary embodiment, the dosing rotational movement—and is additionally secured against rotating by the surrounding coupling member 12, which is also decoupled. As already mentioned, the block is obtained through the slip coupling formed between the coupling member 12 and holding means 2*a* and the rotationally secured engagement between the coupling member 12 and the piston rod 11.

Once the desired dosage has been set, the user injects the injection cannula into and underneath the skin, into the subcutaneous tissue, at the desired injection location. He then triggers the delivery of the dosage set, using the same hand as also holds the injection device while injecting.

The operating button 27, which fulfils the function of a dosing button when setting the dosage, is—in a dual function—also a triggering button. When setting the dosage, the dosing and display member 30 is held in accordance with the dosage latching positions of the latching elements 28 and co-operating latching elements 8 of the slip coupling, i.e. the slip coupling prevents the dosing and display member 30 from moving under the influence of the spring member 32. The coupling between the casing portion 3 and the dosing and display member 30 which exists via the slip coupling at 8, 28 must therefore be released for the delivery. This is achieved by releasing the dosing coupling (formed at 20, 24) by the user pressing the operating button 27 in the distal direction with his thumb. When exerting a corresponding pressure force, the operating button 27 is moved in the distal direction relative to the casing portion 3 and coupling member 22, against the force of the spring 23, and presses against the coupling member 12 in this movement. The coupling member 12 flexes axially inwardly in the region of its integrated spring 13, such that its engaging elements 15a pass into the rotationally secured engagement with the co-operating engaging elements 21 of the coupling member 16. In a transitional phase of the axial movement, the dosing coupling between the coupling member 22 and the coupling member 16 is still closed, while the coupling engagement of the delivery coupling between the coupling member 12 and coupling member 16 has also already been established. However, as soon as the engaging elements 15b contact the axial stopper of the coupling member 12 in the distal direction, the continuing pressure on the operating button 27 causes the coupling member 16 to move in the distal direction, against the force of its spring 17, which axially raises it out of the coupling engagement with the coupling member 22.

As soon as the dosing coupling has been released, the dosing and display member 30 is screwed in the distal direction by the elasticity force of the spring member 32. The rotational movement element of the dosing and display member 30 is transmitted onto the coupling member 16 in the guiding engagement between the guide 18 and the engaging element 31. Due to the closed delivery coupling, the coupling member 16 transmits the rotational movement onto the coupling member 12, which is in turn connected, secured against rotating, to the piston rod 11, such that the piston rod 11 is rotated in the threaded engagement with the holding means 2a and presses the piston 10 in the advancing direction V. The delivery movement of the components involved is terminated by the stopper of the dosing and display member 30 on the shoulder 2c. The stroke or axial element of the adjusting path of the dosing and display member 30 therefore defines the stroke of the piston 10 and thus the dosage delivered. Because the thread pitch of the threads 3a and 30a is larger than the threads of the piston rod 11 and the holding means 2a, the stroke of the dosing and display member 30 is reduced to a stroke of the piston 10 in accordance with the reduction ratio. During the delivery movement, the slip coupling formed between the spring 14 and the holding means 2a generates a clicking noise which is clearly perceptible and acoustically indicates to the user that medicine is being delivered. The delivery operation can also be verified at least in principle through the windows 1b and 2b, on the basis of the axial position of the piston 10.

When setting the dosage, the stopper member 26 is also moved in the threaded engagement with the coupling member 22, in accordance with the dosage set. When the quantity of medicine predetermined by the maximum stroke of the stopper member 26 has been fully administered, which for a completely full reservoir R will not be the case until after a plurality of injections, the user replaces the empty reservoir R with a new, full reservoir R, for which he merely has to separate the casing portion 1 from the proximal casing portion 2, 3, insert the new reservoir R with the piston 10 already accommodated in it, and connect the casing portion 1 and the casing portion 2, 3 back together.

In the exemplary embodiment, all the springs except for the force member 32 are formed as an integral part of a coupling member comprising a coupling part and a spring part, respectively. Alternatively, however, one or more of the springs can be also conventionally formed, separately from the respective coupling member, as a steel spring. The springs 13, 17 and 23 can thus be directly replaced with steel springs, since they exclusively fulfill a spring function. Replacing the spring 14, by contrast, requires a replacement spring and latching elements formed at the distal end of the coupling member 12.

With respect to the arrangement consisting of the dosing and display member 30 and the spring member 32, it may be noted that instead of the dosing and display member 30, the spring member 32 can alternatively be arranged axially overlapping the reservoir R, and is supported on a thrust bearing, for example the shoulder 2c. In such a reversal of the installation arrangements, the dosing and display member 30 would be moved in the proximal direction up to and against a stopper during delivery. In yet another alternative, the spring member 32 can be installed as a tension spring, although installing it as a compression spring may be preferred. Another alternative is also described in German patent applications Nos. 10 2005 043 806.7 and 10 2005 043 807.5. In accordance with these applications, the spring member which is adapted as described to the slip coupling is installed as a torsion spring. The senior applications are hereby incorporated with respect to the adapted arrangement consisting of the slip coupling and the spring member.

Embodiments of the present invention, including preferred embodiments, have been presented for the purpose of illustration and description. They are not intended to be exhaustive or to limit the invention to the precise forms and steps disclosed. The embodiments were chosen and described to provide the best illustration of the principles of the invention and the practical application thereof, and to enable one of ordinary skill in the art to utilize the invention in various embodiments and with various modifications as are suited to the particular use contemplated. All such modifications and variations are within the scope of the invention as determined by the appended claims when interpreted in accordance with the breadth they are fairly, legally, and equitably entitled.

The invention claimed is:

1. An injection device for injecting a substance, the device comprising:
   a casing comprising a reservoir for the substance;
   an operating button for selecting a dosage of the substance to be injected, said button moveable relative to the casing in a dosing movement and a correction movement opposite to the dosing movement;
   a slip coupling comprising co-operating latching elements engageable with each other and coupling the operating button to the casing in discrete latching positions during the movements of the operating button; and
   a spring member which opposes the movement of the operating button in at least one of the movements;
   wherein one of the latching elements is shaped asymmetrically with respect to the two movements in which the latching elements can be moved relative to each other such that when the latching elements are engaged in the dosing movement and the correction movement, there is a lower resistance to movement of the operating button in one of the movements than in the other movement.

2. The injection device according to claim 1, wherein the spring member is one of a compression spring or a torsion spring.

3. An injection device, comprising:
   a) a casing with a reservoir for an injectable product;
   b) an operating button for setting a product dosage which can be moved relative to the casing in a dosing direction which increases the dosage and in a correcting direction opposite the dosing direction;
   c) a conveying member for delivering the dosage set;

d) a slip coupling comprising a latching element and a co-operating latching element which latch to each other in a latching engagement and couple the operating button to the casing in discrete latching positions during a movement in the dosing direction and the correcting direction; and e) a spring member which opposes the movement of the operating button in at least one of the directions; wherein f) the latching element or co-operating latching element are shaped with flanks that are asymmetrical with respect to the two directions, wherein a first flank of the element points in one of the two directions and is steeper than a second flank of the same element which points in the other direction such that in the latching engagement, the second flank offers a lower resistance to the movement in one of the directions than a resistance the first flank offers to the movement in the other direction.

4. The injection device according to claim 3, wherein the spring member is or can be coupled to the conveying member and drives the conveying member during delivery.

5. The injection device according to claim 4, wherein the spring member is decoupled from the conveying member when the dosage is being set and can be coupled to the conveying member by a delivery coupling for the delivery.

6. The injection device according to claim 3, wherein the spring member is more highly tensed from latching position to latching position during the movement of the operating button in one direction.

7. The injection device according to claim 3, wherein the spring member opposes movement in the dosing direction with a spring force.

8. The injection device according to claim 3, wherein the slip coupling comprises a first coupling half comprising the latching element and a second coupling half comprising the co-operating latching element, and one of the coupling halves can be rotated relative to the other about a rotational axis.

9. The injection device according to claim 8, wherein the latching element and the co-operating latching element radially engage with each other in the latching engagement with respect to the rotational axis.

10. The injection device according to claim 8, wherein the latching element and the co-operating latching element axially engage with each other in the latching engagement with respect to the rotational axis.

11. The injection device according to claim 3, wherein the slip coupling comprises a first coupling half comprising the latching element and a second coupling half comprising the co-operating latching element, and the latching element and the co-operating latching element directly engage with each other in the latching engagement.

12. The injection device according to claim 11, wherein one of the coupling halves can be moved relative to the other in the dosing direction and in the correcting direction.

13. The injection device according to claim 3, wherein the flanks of the latching element or the co-operating latching element is or are shaped asymmetrically with respect to the dosing direction such that the second flank offers the lower resistance to movement of the operating button in the dosing direction.

14. The injection device according to claim 3, wherein the slip coupling comprises a coupling spring that opposes a release of the latching engagement with a restoring spring force and either the latching element or the co-operating latching element is formed on or attached to the coupling spring.

15. The injection device according to claim 14, wherein the slip coupling comprises a first coupling half comprising the latching element and a second coupling half comprising the co-operating latching element, and the coupling spring is formed on or attached to at least one of the coupling halves.

16. The injection device according to claim 15, wherein one of the coupling halves can be rotated relative to the other about a rotational axis, and the coupling spring is an elastically, radially, flexible flexing spring.

17. The injection device according to claim 15, wherein the coupling spring is formed as a flexing spring on one of the coupling halves and is fixedly clamped at both ends to the coupling half.

18. The injection device according to claim 14, wherein one of the operating button or the casing comprises a ring or partial ring comprising ring segments arranged successively in the circumferential direction, one of which forms the coupling spring and the other of which forms a comparatively stiffer ring segment, and each end of the coupling spring is fixedly clamped to one of the comparatively stiffer ring segments.

19. The injection device according to claim 18, wherein the ring or partial ring comprises elastic first ring segments which are alternately arranged successively in the circumferential direction, and comparatively stiffer second ring segments, and the first ring segments each form the coupling spring.

20. The injection device according to claim 3, wherein a plurality of latching elements or co-operating latching elements are provided, and each latching element or co-operating latching element is provided with a coupling spring.

21. The injection device according to claim 3, wherein the slip coupling comprises a plurality of latching elements or a plurality of co-operating latching elements which latch to each other in the latching engagement and can be moved relative to each other in a coupling dosing direction which increases the dosage and in an opposite coupling correcting direction.

22. The injection device according to claim 3, wherein the operating button is coupled to a dosing member, and the dosing member can be moved to and against a delivery stopper when delivering the dosage and away from the delivery stopper, against the spring force of the spring member, for setting the dosage.

23. The injection device according to claim 22, wherein the operating button and the dosing member are releasably coupled to each other by a dosing coupling.

24. The injection device according to claim 22, wherein the dosing member is decoupled from the conveying member when the dosage is being set and can be coupled to the conveying member by a delivery coupling for the delivery.

25. The injection device according to claim 3, wherein the latching element is formed on or attached to the operating button.

26. The injection device according to claim 3, wherein the co-operating latching element is formed on or attached to the casing.

27. The injection device according to claim 3, wherein the co-operating latching element is formed on or attached to a member which is guided such that it can be moved axially relative to the casing but is secured against rotating, and on which the spring member is supported.

28. The injection device according to claim 3, wherein the operating button can be rotationally moved relative to the casing for setting the dosage.

29. The injection device according to claim 28, wherein the operating button forms a trigger for delivery and can be translationally moved relative to the casing in an injection direction.

* * * * *